United States Patent
Zakin et al.

[11] Patent Number: 5,145,645
[45] Date of Patent: Sep. 8, 1992

[54] CONDUCTIVE POLYMER SELECTIVE SPECIES SENSOR

[75] Inventors: Mitchell R. Zakin, Bradford; Lawrence S. Bernstein, Lexington, both of Mass.; Richard A. Moody, Nashua, N.H.

[73] Assignee: Spectral Sciences, Inc., Burlington, Mass.

[21] Appl. No.: 710,240

[22] Filed: Jun. 3, 1991

Related U.S. Application Data

[63] Continuation of Ser. No. 539,030, Jun. 15, 1990, abandoned.

[51] Int. Cl.$^5$ .................. G01N 27/04; H01C 7/00
[52] U.S. Cl. ........................... 422/98; 422/58; 422/88; 422/90; 436/902; 73/31.05; 73/31.01; 338/13; 338/34
[58] Field of Search .......... 422/83, 88, 90, 82.02, 422/58, 98; 436/151, 149, 902; 73/31.01, 31.05; 338/13, 27, 34, 35

[56] References Cited

U.S. PATENT DOCUMENTS

| 4,423,407 | 12/1983 | Zuckerman | 422/98 |
| 4,542,640 | 9/1985 | Clifford | 73/31.05 |
| 4,638,286 | 1/1987 | Nichols | 73/25.03 |
| 4,638,443 | 1/1987 | Kaneyasu et al. | 73/31.05 |
| 4,910,149 | 3/1990 | Okube et al. | 436/57 |

FOREIGN PATENT DOCUMENTS

| 0108651 | 7/1982 | Japan | 73/31.05 |
| 6227161 | 11/1985 | Japan | |
| 613040 | 1/1986 | Japan | |
| 63-21596 | 9/1988 | Japan | |

Primary Examiner—Robert J. Warden
Assistant Examiner—T. A. Trembley
Attorney, Agent, or Firm—Iandiorio & Dingman

[57] ABSTRACT

A selective chemical species detector including a conductive polymer based sensing element having a detectable characteristic, for example, the polymer resistivity, permanently altered on exposure to a first chemical species and not permanently altered on exposure to a second chemical species. The detector then determines a permanent change in the detected characteristic and indicates the presence of a chemical species on detection of a such a permanent characteristic change. Also disclosed is a method of fabricating such a sensing element to achieve the desired selectivity.

15 Claims, 4 Drawing Sheets

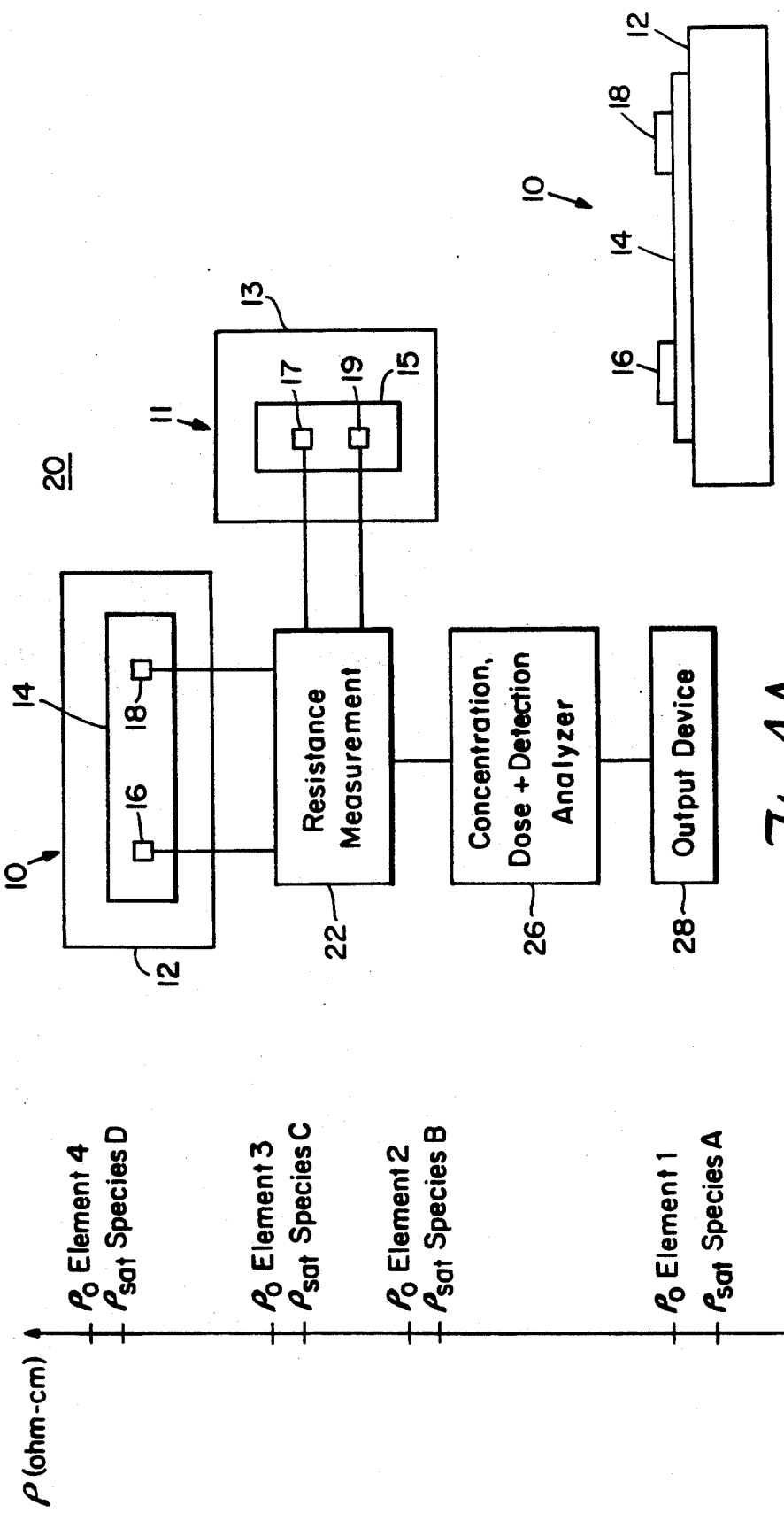

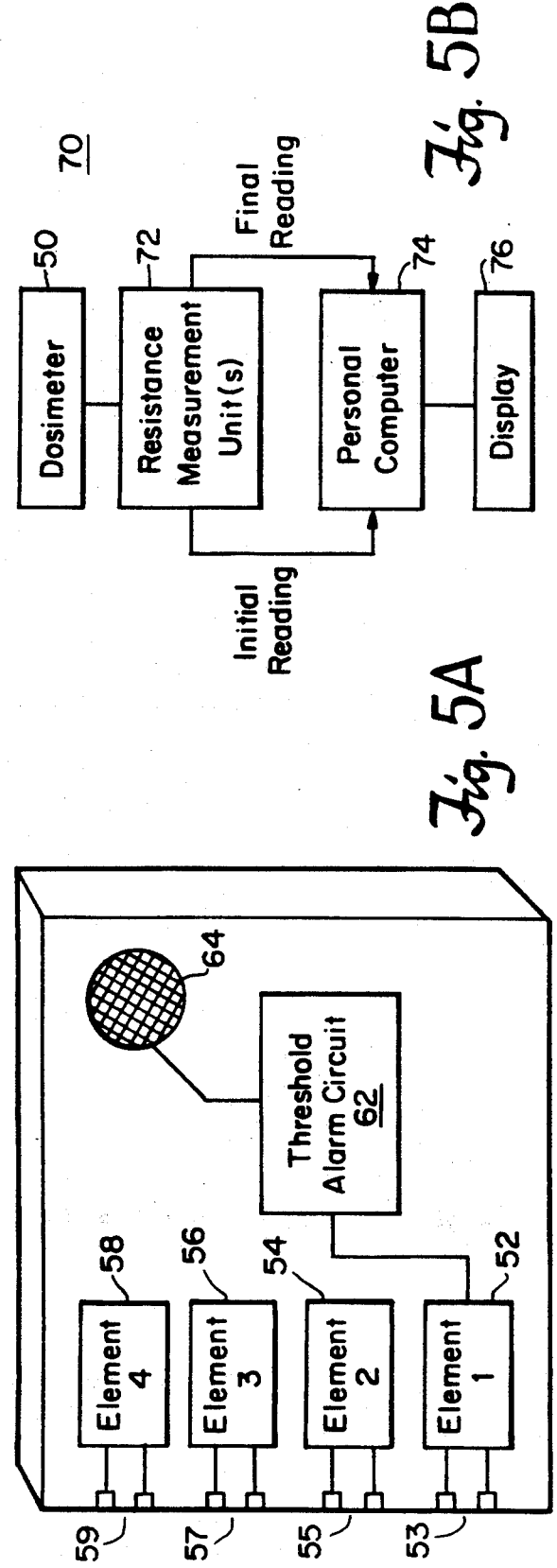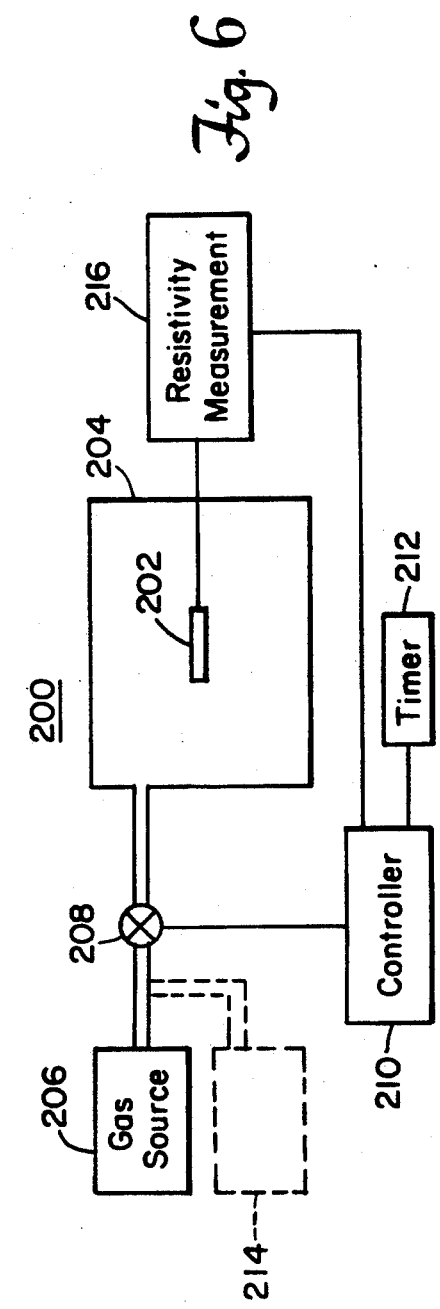

CONDUCTIVE POLYMER SELECTIVE SPECIES SENSOR

GOVERNMENT RIGHTS

The invention was made with government support under Contract No. FO4701-89-C-0054 awarded by the United States Air Force. The government has certain rights in the invention.

This is a continuation of application Ser. No. 07/539,030, filed Jun. 15, 1990.

FIELD OF INVENTION

This invention relates to a conductive polymer based selective chemical species sensor.

BACKGROUND OF INVENTION

Accurate selective detection and quantification of chemical species has to date not been achievable at a relatively low cost. Paper tape sensors coated with a compound which changes color when exposed to a chemical species can be relatively inexpensive. However, the tape coating layer may respond to a number of species, making selectivity difficult. In addition, the color change may be indicated at an extremely low concentration for one species, and a relatively high concentration for other species. In that case, the presence of a trace amount of the first species could be detected as a significant quantity of the second species. Since many species are present in the atmosphere in trace amounts, the potential for interference or false readings with these paper tape devices is thus significant.

Another category of relatively inexpensive chemical sensors are solid state devices, such as metal oxide films, which display a conductivity change in the presence of certain chemical species, but only at elevated temperatures. The solid state sensors are often used to detect toxic gases. Although adequate for the gross detection of certain species, these metal oxide sensors are typically responsive to many gases, leading to problems with accuracy and selectivity. In addition, because the devices operate at a high temperature, they require a power source for heating and can degrade quickly.

The sensing techniques which have the required sensitivity and selectivity are typically extremely sophisticated, expensive scientific instruments which need to be operated by a skilled technician. For example, mass spectrometers are very sensitive and can achieve the desired selectivity, unless two or more species present in the sample give rise to ions with the same mass to charge ratio. Spectroscopic techniques in principle can achieve the desired selectivity and sensitivity as long as there is no overlap in the species' spectroscopic features, but the instruments typically cost tens of thousands of dollars.

SUMMARY OF INVENTION

It is therefore an object of this invention to provide a low cost selective species sensor which is extremely sensitive and selective.

It is a further object of this invention to provide such a sensor which can be tailored to selectively sense one or more species.

It is a further object of this invention to provide such a sensor in which selectivity is achieved by altering the initial resistivity of the conductive polymer sensing element.

It is a further object of this invention to provide such a sensor which can selectively detect species as well as determine their concentration and/or dose.

This invention results from the realization that by changing the initial resistivity of a conductive polymer based sensing element, the chemical species to which the element is responsive may be selected to achieve selective species detection and quantification, and further that a number of such elements may be used for selective detection and quantification of more than one species.

A selective chemical species detector according to this invention may be accomplished with a sensor having a conductive polymer based sensing element with a detectable characteristic permanently altered on exposure to a first chemical species and effectively unaltered (either unaltered or reversibly altered) on exposure to a second chemical species, means for detecting a change in the characteristic, and means responsive to the detected change for indicating the presence of a chemical species on detection of a permanent change in the characteristic. Preferably, the characteristic is an electrical characteristic, which may be the conductive polymer resistivity or conductivity.

In a preferred embodiment, the detector includes a plurality of discrete conductive polymer based sensing elements, each with a detectable characteristic permanently altered on exposure to at least one chemical species and effectively unaltered on exposure to at least one other chemical species. The sensed species may be polymer material dopants, or polymer material compensating agents. Preferably, a first element is responsive to at least a first species, a second element is responsive to a second species and not responsive to the first species, a third element is responsive to a third species and not responsive to the first and second species, and so forth, for bracketing the species to be detected for selective detection and quantification of a number of species.

The invention may further include means, responsive to the means for detecting the characteristic change of the conductive polymer sensing element, for resolving the dose of the chemical species. That may be accomplished by including means for determining the value of the element electrical characteristic, and comparing the change in the determined value to a predetermined relationship between the species dose and the electrical characteristic. There may further be included means for resolving the average concentration of a detected species, including means for determining the time of the sensor exposure to the chemical species and dividing the dose by the exposure time to determine the average concentration.

This invention may also be accomplished in a method of fabricating a selective species sensing element including providing a conductive polymer material, establishing the material saturation resistivity toward at least one species, and altering a polymer electrical characteristic, such as the resistivity or conductivity, to alter the chemical species to which the material permanently responds. The electrical characteristic may be altered with a polymer dopant or compensating agent. Preferably the material is polyaniline, polythiophene, polypyrrole, polyacetylene, or polydiacetylene, or a derivative thereof.

DISCLOSURE OF PREFERRED EMBODIMENT

Other objects, features and advantages will occur to those skilled in the art from the following description of a preferred embodiment and the accompanying drawings, in which:

FIG. 2 is a chart of the saturation resistivities of a conductive polymer for four different chemical species illustrating a selective detection technique using the device of this invention;

FIG. 3 is a side elevational, schematic view of a selective species sensing element of the sensor according to this invention;

FIG. 4A is a schematic diagram of a multi-species selective sensor according to this invention employing two sensing elements such as that shown in FIG. 3;

FIG. 5A is a schematic diagram of an alarm and dosimeter device employing the sensing elements according to this invention;

FIG. 5B is a block diagram of a measurement and output device for the dosimeter of FIG. 5A; and FIG. 6 is a schematic diagram of a device for doping polymer elements for practicing the method of this invention.

Conductive polymers are polymers whose backbones or pendant groups are responsible for the generation and propagation of charge carriers. These polymers typically exhibit dramatic changes in resistivity on exposure to certain chemical species. The change may be permanent or impermanent (reversible). Many species have no effect on polymer resistivity. Typically, the resistivity of the virgin or doped conductive polymers decreases dramatically and irreversibly with exposure to dopant species. As an example, polyaniline may have a bulk resistivity of $10^{10}$/ohm-centimeter. When a 1 mil thick film of polyaniline is exposed to pure hydrogen chloride gas dopant for about one minute, or 1N aqueous HCl solution for about fifty-five hours, its resistivity decreases to approximately 10/ohm-centimeter. Likewise, the doped conductive polymer resistivity increases dramatically on exposure to a compensating agent.

This invention may be accomplished in a selective chemical species detector employing one or more conductive polymer based sensing elements with a detectable characteristic, such as the polymer resistivity or conductivity, which is permanently altered on exposure of the sensor element to one or more chemical species, and effectively unaltered (either unaltered or only non-permanently (reversibly) altered) on exposure to one or more different chemical species, to accomplish selective chemical species detection based on the change in the detected characteristic. For selective quantification of n chemical species, n such conductive polymer based sensing elements may be provided, each having an initial resistivity established according to the polymer saturation resistivities for the species being detected, as will be more fully explained below.

Figure 1A:
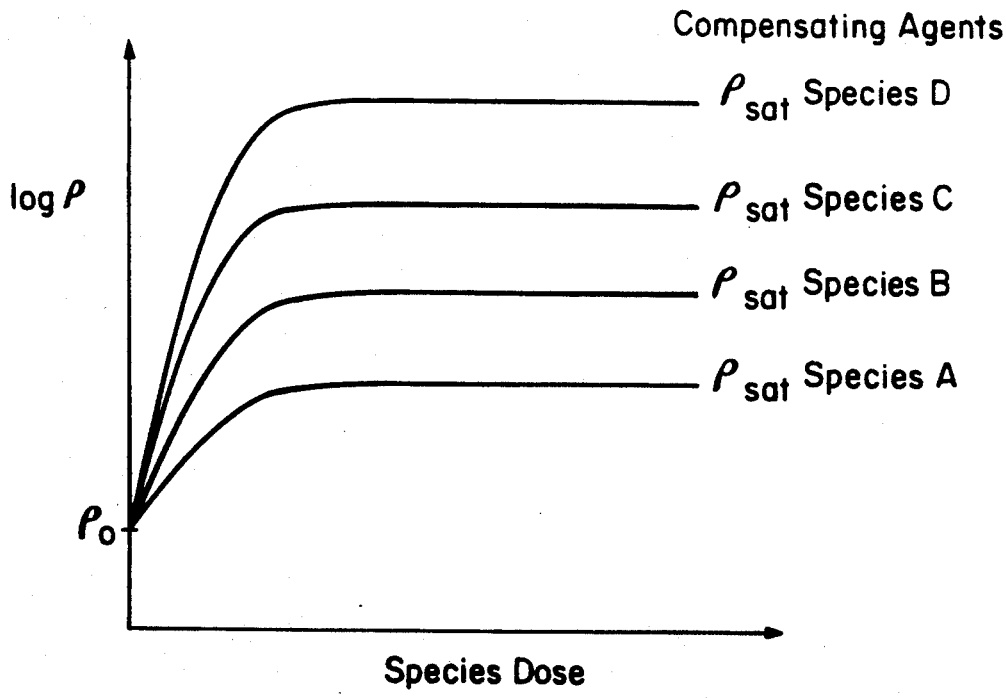
FIGS. 1A and 1B are curves illustrating the response of the resistivity of a conductive polymer to a series of compensating agents and dopants, respectively.
Figure 1B:
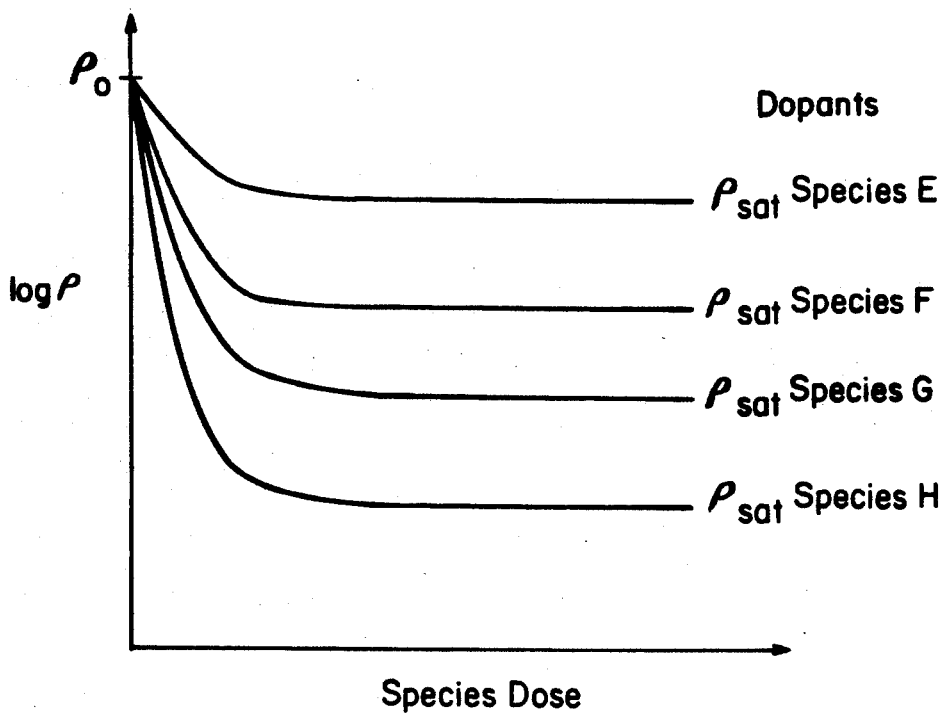

FIGS. 1A and 1B illustrate the irreversible response of the resistivity of a conductive polymer material to compensating agents and dopants, respectively. Dopants are species which decrease the resistivity of an undoped or doped conductive polymer, and compensating agents are species which increase the resistivity of a previously doped conductive polymer.

What is shown in FIG. 1A is a plot of the resistivity versus dose for four hypothetical compensating agent species, labelled A, B, C and D. As shown in that figure, the resistivity of previously doped conductive polymers such as polyaniline, polyacetylene, polydiacetylene, polypyrrole, polythiophene, and their derivatives, increases from an initial value designated as $\rho 0$ to a saturation value p sat with increasing compensating species dose. The $\rho$sat value is fully defined by the conductive polymer material, the dopant, and the species to be detected; i.e., the saturation resistivity is an absolute upper limit to the resistivity of a given doped conductive polymer material exposed to a given compensating agent.

Similarly, FIG. 1B illustrates the change in resistivity of conductive polymer materials in relation to species dose for hypothetical dopant species E, F, G, and H. These curves illustrate that in the presence of dopant species the resistivity of conductive polymers decreases to a lower limit, also designated as $\rho$sat, which is fully defined by the conductive polymer material and the species.

The change in material resistivity illustrated in FIGS. 1A and 1B is permanent; on removal of the material from the presence of the chemical species, the final resistivity level does not change. As an example of the dramatic effect of the species on the resistivity of the conductive polymer material, and the permanence of the resistivity change, an undoped polythiophene sample exposed to $NOPF_6$ exhibited a resistivity change from the undoped to saturated condition of approximately ten orders of magnitude. Accelerated aging tests in humid ambient air at elevated temperatures indicate that the resistivity of this doped material will increase by no more than 10% over a one-year period. When this doped polythiophene sample was exposed to a compensating agent such as hydrazine, the resultant change in resistivity showed similar permanence toward subsequent exposure to humid air.

The irreversibility and stability of the resistivity change in the conductive polymers allows the materials to be used for both detection (determination of environmental presence) and quantification (determination of dose and/or average concentration) of chemical species. As illustrated, a given doped or undoped polymer material has a unique response to dopants and compensating agents dependent on the species dose. Also, because the $\rho$sat of a given polymer material exposed to a given chemical species is known, the material may be made sensitive to that species by establishing its initial resistivity before exposure, $\rho 0$, below the $\rho$sat, and may be made insensitive to the species by establishing a $\rho 0$ above the $\rho$sat. This concept enables the quantification of n species by use of an array of n polymer elements with properly graded initial resistivities. Detection of one or more species may be accomplished with one or more such elements, dependent on the polymer materials used, the saturation resistivities, and the element initial resistivities.

Because the polymer resistivity is uniquely determined by the species dose, any species causing a permanent resistivity change may be quantified by measuring the initial polymer resistivity $\rho 0$, and the altered resistivity $\rho$final. The resistivity change can then be related to the species dose using a predetermined polymer-species calibration curve such as those illustrated in FIGS. 1A and 1B. If the exposure time is known, the average species concentration can be determined from the dose by dividing the dose by the exposure time. For quantification of n known species (in any phase), n conductive polymer samples are employed.

These principles may be applied to selective detection and quantification of conductive polymer dopants and compensating agents. FIG. 2, which is a plot of the saturation resistivity of a hypothetical doped polymer when exposed to compensating agents A, B, C and D, illustrates the principle of a three-species detection and quantification scheme. Similar principles will apply to the detection and quantification of dopants. Plotted on the resistivity scale is the initial resistivity $\rho 0$ of four conductive polymer sensing elements, labelled 1, 2, 3 and 4. Preferably, the initial resistivity values of elements 1 through 4 are set so that, for each species desired to be sensed (in this case B, C and D), there is a single sensing element having an initial resistivity just above the saturation resistivity of the species with the next lowest saturation resistivity; in other words, each species to be sensed is bracketed on the resistivity scale by two sensing elements.

For example, the resistivity of sensing element 1 is set just above the saturation resistivity for species A, element 2 just above $\rho sat$ for species B, and so forth. The sensor then determines the permanent (irreversible) change in resistivity of each of the sensing elements. If species A is present, none of the sensing elements will show such a change in resistivity, i.e., species B, C and D can be quantified in the presence of any concentration of any interferent species such as A whose $\rho sat$ falls below that of element 1. If only species B is present, only element 1 will show a permanent increase in resistivity, the final resistivity falling somewhere between the initial value and $\rho sat$ for species B. If species C is present, both elements 1 and 2 will show a permanent increase in resistivity, regardless of the presence of species B. If species D is present, elements 1, 2 and 3 will show a permanent change in resistivity. Element 4 is employed in this example as a control to detect species with $\rho sat$ greater than that of species D; its resistivity will not permanently change no matter which of the four species A-D is present.

In order to achieve full selectivity and quantification, it is important that none of the conductive polymer sensing elements reach a saturation value for a species being sensed, as the element resistivity can not permanently increase above this value regardless of the species dose. If an element does reach saturation for a given species, the sensor will have lost the ability to differentiate the presence of that species from the presence of any other species having a higher $\rho sat$. Also, it is important to choose initial element resistivities which are spaced far enough below the next-closest species saturation resistivity to provide the maximum possible sensor measurement dynamic range.

Presuming these conditions are met, it is possible to sense the presence and determine the dose and average concentration of n species with n such conductive polymer sensing elements having the relationship to the species saturation resistivities such as that shown in FIG. 2. It is only necessary to establish a priori the responses of the conductive polymer material(s) to be used in the sensing elements to each of the species being detected, and each polymer-species saturation resistivity, in order to fully identify and quantify one or more species in a mixture of species. The presence of species causing no change or only reversible changes to the polymer resistivity has no effect on the measurements made.

For example, if only species B and C are present, the dose of species C is fully determined by the permanent change in resistivity of element 2. Thus, the resistivity change of element 1 (due to both species B and C), combined with the dose of species C (as determined from element 2), determines uniquely the dose of species B.

FIG. 3 depicts chemical species sensing element 10 according to this invention, employing conductive polymer based sensing film 14 on electrically insulating supporting substrate 12. Spaced conductive electrodes 16 and 18 contact film 14.

FIG. 4A depicts schematically the use of element 10 in a conductive polymer selective species sensor 20 according to this invention; sensor 20 is capable of simultaneously and selectively detecting and quantifying up to two species. Conductive electrodes 16 and 18 of chemically sensitive element 10 are electrically connected to resistance measurement device 22. Similarly, electrodes 17 and 19 on the surface of conductive polymer film 15 supported by substrate 13, making up sensing element 11, are also electrically connected to resistance measuring device 22, which measures the resistance of conductive polymer films 14 and 15 between electrodes 16 and 18, and 17 and 19, respectively. It should be understood that the sensing element electrodes must be spaced apart and in contact with the polymer, but need not be on the surface of the polymer material; they may be buried within or below the polymer. It should also be understood that the sensing elements may be made of the same or different polymer materials as desired. Also, different dopants may be used to tailor the initial element resistivities, their species sensitivity, and their saturation resistivities, as desired to accomplish a desired detection/quantification scheme.

Device 22 may measure resistance at any frequency. The change in conductive polymer material resistance is related to the dose of the dopant or compensating species present as described above. Concentration, dose, and detection analyzer 26 converts the resistance measurements to the dose and/or concentration of the detected species for display on output device 28. A permanent resistivity change of any magnitude may also be used to indicate the species' presence.

Figure 4B:
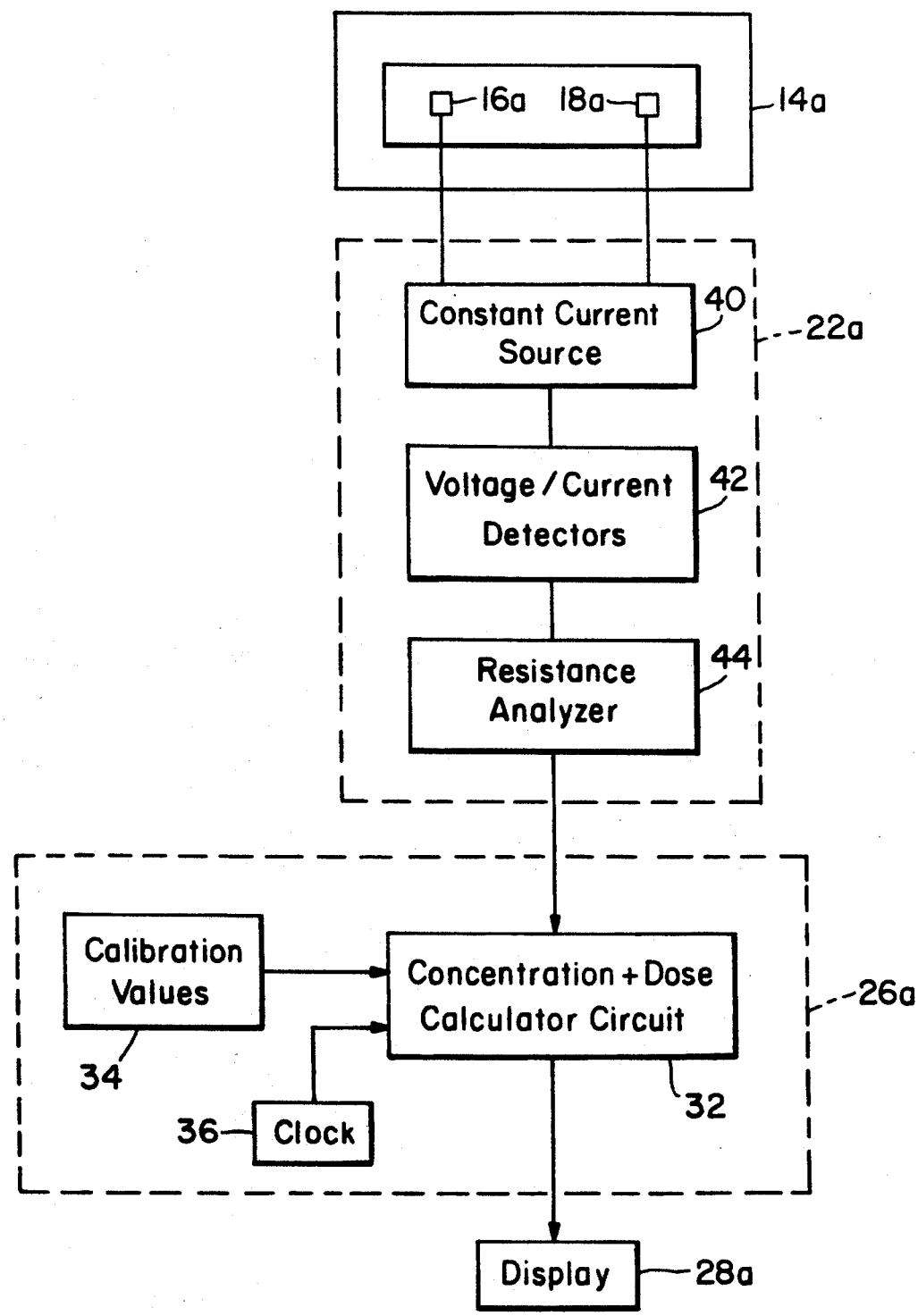
FIG. 4B is a more detailed schematic diagram of the resistance measurement device and the concentration, dose and detection analyzer of the sensor of FIG. 4A.

Resistance measurement device 22a and concentration and dose analyzer 26a are shown in more detail in FIG. 4B. Resistance measurement device 22a includes constant current source 40 for passing a specified current between electrodes 16a and 18a through conductive polymer film 14a. Voltage/current detectors 42 measure the voltage drop and current across the electrodes, respectively, with film resistance determined by resistance analyzer 44 using Ohm's law.

Film resistance data is passed to concentration and dose calculator 32, which is also responsive to calibration values 34, and clock 36. By including lookup tables or calibration curves at least for the species being detected in element 34, the dose and/or average concentration of the species to be quantified may be determined from the resistance measurements. Clock 36 provides a time base for determining resistance change with time, which may be used, for example, in calculating the average concentration from the dose. Display 28a can then display any or all of the calculated values, as well as the species' presence.

One practical embodiment of the selective species sensor according to this invention is illustrated in FIGS. 5A and 5B. Dosimeter badge 50 includes conductive polymer based sensing elements 1, 2, 3 and 4 for sensing species B, C and D, FIG. 1A. The elements have associated therewith electrode sets 53, 55, 57 and 59, respectively. Device 50 may be used to detect the presence and dose of species B, C and D as follows: sensing element 1 has its initial resistivity $\rho 0$ set just above the $\rho sat$ of species A, FIG. 1A. As a result, the resistivity of element 1 will increase on exposure to any or all of species B, C and D. Element 2 has its initial resistivity $\rho 0$ set just above the $\rho sat$ value for species B; as a result, element 2 undergoes no permanent resistivity change in the presence of species A or B, but does undergo such a change in the presence of species C and/or D. Similarly, element 3 has its initial resistivity set just above the $\rho sat$ of species C. As a result, element 3 is responsive only to species D. Element 4 is not responsive to any of species A through D, and is included as a control, for detection of the presence of any interfering chemical species with a $\rho sat$ above that of species D.

Threshold alarm circuit 62 is responsive to element 1 for indicating an alarm condition through visual or audio alarm 64 when the resistivity of element 1 increases from its initial value $\rho 0$ to a preset threshold value indicative of a desired total dose of species B, C, and/or D.

Detection and measurement system 70 employing dosimeter 50 is illustrated in FIG. 5B. Resistance measurement unit 72 is employed to measure the initial resistance of polymer elements 1 through 4 of dosimeter 50. These polymer resistance values are stored in personal computer 74, which also may be used to track elapsed time, and has in its memory the calibration curves or lookup tables for comparison to the measured resistivity for calculation of species dose and/or concentration. After the exposure, the resistance of elements 1 through 4 is again measured, and the change in resistivity is determined and then related to species dose by comparison to the calibration curves. The readings are displayed on display 76.

An example of a group of compensating agents which may be detected and quantified with the device of this invention includes unsymmetrical dimethylhydrazine (UDMH), hydrazine, and monomethylhydrazine (MMH). Polythiophene may be used as the conductive polymer material and $NOPF_6$ may be used to set the initial resistivities of the elements to the desired values.

Since ammonia is typically present with this group, all of the sensing elements are made ammonia-insensitive by setting their initial resistivities, $\rho o$, above the $\rho sat$ for ammonia; approximately $1.5 \times 10^3$ ohm-cm, using $NOPF_6$. UDMH has the next highest $\rho sat$ at $1.5 \times 10^5$ ohm-cm, followed by hydrazine at $3.0 \times 10^5$ ohm-om and MMH at $8.5 \times 10^5$ ohm-om. If the initial resistivity of element 1, FIG. 5A, is set to be just above $1.5 \times 10^3$ ohm-cm, element 1 is responsive to UDMH, hydrazine, and MMH. The initial resistivities of elements 2, 3 and 4 are likewise set just above $1.5 \times 10^5$, $3.0 \times 10^5$, and $8.5 \times 10^5$ ohm-cm, respectively. Element 2 is then sensitive to hydrazine and MMH, element 3 only to MMH, and element 4 may be used as the control. None of the elements are sensitive to ammonia.

The resistivities of elements 1 through 4 are measured before and after exposure to determine the change in resistivity of each element. The doses of the species are then determined in the manner previously described. Element 1 may also be used as a "hydrazine group" alarm based on a preset threshold in element resistivity.

The sensing elements may be fabricated by choosing a polymer material and dopant/compensating agent to accomplish the desired detection. The material is doped to establish the initial resistivity, $\rho 0$. For example, FIG. 6 illustrates device 200 for doping conductive polymer sample 202, contained within enclosure 204. The dopant species is supplied by gas source 206, flow-controlled by valve 208 operated by controller 210. Timer 212 may be employed to control dopant exposure time for controlling the resistivity of the sample. Sample 202 may be masked to expose only one surface if desired. Dopant species concentration may be controlled, if desired, by including alternate source 214, shown in phantom, controlled in like manner. Resistivity measurement device 216 may be employed to continuously measure the resistivity of element 202 as it is doped; controller 210 may then stop the flow of dopant, or indicate the end of the dopant period, when the element resistivity is as desired. Doping may also be accomplished by exposure to a dopant solution.

Although specific features of the invention are shown in some drawings and not others, this is for convenience only as each feature may be combined with any or all of the other features in accordance with the invention.

Other embodiments will occur to those skilled in the art and are within the following claims:

What is claimed is:

1. A fast response selective chemical species dosimeter, comprising:
   a sensor with a first conductive polymer based sensing element having its resistivity permanently altered on exposure to at least a first chemical species in a first group of species and not permanently altered on exposure to at least a first chemical species in a second group of species;
   means for detecting and quantifying any permanent change in the resistivity of said first conductive polymer based sensing element; and
   means, responsive to said means for detecting and quantifying, for resolving from the permanent change in element resistivity the dose of a chemical species of said first group.

2. The dosimeter of claim 1 in which said sensor includes a plurality of discrete conductive polymer based sensing elements, each with its resistivity permanently altered on exposure to at least one first chemical species and not permanently altered on exposure to at least one other chemical species for selective resolution of the dose of a plurality of species.

3. The dosimeter of claim 2 in which said sensor includes a second conductive polymer based sensing element having its resistivity permanently altered on exposure to at least a second chemical species in said first group of species and not permanently altered on exposure to said first chemical species in said first group and said first chemical species in said second group.

4. The dosimeter of claim 3 in which said sensor includes a third conductive polymer based sensing element having its resistivity permanently altered on exposure to at least a third chemical species in said first group and not permanently altered on exposure to said first and second chemical species in said first group and said first chemical species in said second group.

5. The dosimeter of claim 2 in which said sensor includes n discrete conductive polymer based sensing elements, in which the resistivity of no two of said conductive polymer based sensing elements is permanently altered by the same chemical species and in which the resistivity of no two of said conductive polymer based sensing elements is impermanently altered by the same chemical species, for selective resolution of the dose of n chemical species.

6. The detector of claim 2 in which said sensor includes conductive polymer based sensing elements made from at least two different conductive polymer materials.

7. The detector of claim 2 in which said sensor includes conductive polymer based sensing elements doped with at least two different dopant species.

8. The dosimeter of claim 1 in which said means for resolving the dose includes means, responsive to said means for detecting and quantifying, for comparing the element resistivity to a predetermined relationship between the detected chemical species dose and the conductive polymer resistivity.

9. The dosimeter of claim 1 further including means, responsive to said means for detecting and quantifying, for resolving the average concentration of the chemical species causing the permanent resistivity change.

10. The dosimeter of claim 9 in which said means for resolving the average concentration includes means for determining the time of sensor exposure to the chemical species causing the permanent resistivity change.

11. The detector of claim 10 in which said means for resolving the concentration further includes means for dividing the dose by the exposure time.

12. A fast response selective chemical species dosimeter for determining the dose of species in a group of species, comprising:
- at least two conductive polymer based sensing elements, the resistivity of a first conductive polymer based sensing element falling between the polymer saturation resistivities for first and second species in a group of species and the resistivity of a second conductive polymer based sensing element falling between the polymer saturation resistivities for said second and a third species in said group;
- means for detecting and quantifying any permanent change in resistivity of said first and second conductive polymer based sensing elements; and
- means, responsive to said means for detecting and quantifying, for resolving the dose of at least one of said first, second and third species.

13. A first response selective chemical species dosimeter, comprising:
- a plurality of conductive polymer based sensing elements in which the resistivity of at least a first said conductive based sensing element is permanently changed on exposure to a first of a group of chemical species and not permanently changed on exposure to a second one of said group of chemical species, and in which the resistivity of at least a second, other said conductive polymer based sensing element is permanently changed on exposure to said first and second chemical species;
- means for detecting a permanent change in resistivity of said plurality of conductive polymer based sensing elements;
- means for determining the presence and dose of said first chemical species when the resistivity of both said first and said second conductive polymer based sensing elements changes; and
- means for determining the presence and dose of said second chemical species when the resistivity of said first conductive polymer based sensing element is not permanently changed and the resistivity of said second conductivity polymer based sensing element permanently changes, to selectively detect and determine the dose of the first and second chemical species.

14. A fast-response chemical species dosimeter for determining the dose of first and second species in a group of species, comprising:
- a first sensing element made from a conductive polymer material and having a resistivity lower than the conductive polymer material first and second species saturation values;
- a second sensing element made from the same conductive polymer material as the first sensing element and having a resistivity above the conductive polymer material as the first sensing element first species saturation value and below the conductive polymer material second species saturation value;
- means for detecting a permanent increase in resistivity of said first and second sensing elements;
- means for determining the dose of the first species based on a permanent increase in the resistivity of said first sensing element and no concurrent permanent change in the resistivity of said second sensing element; and
- means for determining the dose of the second species based on a permanent increase in the resistivity of both said first and second sensing elements.

15. A fast-response chemical species dosimeter for selectively determining the dose of first and second species in a group of species, comprising:
- a first sensing element made from a conductive polymer material and having a resistivity higher than the conductive polymer material first and second species saturation values;
- a second sensing element made from the same conductive polymer material as the first sensing element and having a resistivity below the conductive polymer material first species saturation value and above the conductive polymer material second species saturation value;
- means for detecting a permanent decrease in resistivity of said first and second sensing elements;
- means for determining the dose of the first species based on a permanent decrease in the resistivity of said first sensing element and no concurrent permanent change in the resistivity of said second sensing element; and
- means for determining the dose of the second species based on a permanent decrease in the resistivity of both said first and second sensing elements.

* * * * *